United States Patent

Arndt et al.

[11] Patent Number: 4,479,822
[45] Date of Patent: Oct. 30, 1984

[54] SUBSTITUTED CARBANILIC ACID ESTERS AND HERBICIDAL COMPOSITION CONTAINING SAME

[75] Inventors: Friedrich Arndt; Heinrich Franke; Erich Schmidt; Reinhold Puttner, all of Berlin, Fed. Rep. of Germany

[73] Assignee: Schering Aktiengesellschaft, Berlin and Bergkamen, Fed. Rep. of Germany

[21] Appl. No.: 406,897

[22] Filed: Aug. 10, 1982

Related U.S. Application Data

[63] Continuation of Ser. No. 138,577, Apr. 8, 1980, abandoned.

[30] Foreign Application Priority Data

Apr. 5, 1979 [DE] Fed. Rep. of Germany ....... 2913976

[51] Int. Cl.³ .................. C07C 125/065; A01N 37/44
[52] U.S. Cl. ........................................ 71/111; 560/27
[58] Field of Search ..................... 560/27; 71/108, 111

[56] References Cited

U.S. PATENT DOCUMENTS 4,088,474  5/1978  Matterstock et al. ............... 71/108
4,093,447  6/1978  Metzger et al. ...................... 71/111
4,230,483  10/1980  Felix ..................................... 71/100

Primary Examiner—Bernard Helfin
Attorney, Agent, or Firm—Michael J. Striker

[57] ABSTRACT

A substituted carbanilic acid ester of the formula

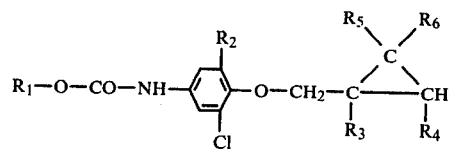

wherein $R_1$ is $C_1$–$C_6$-alkyl, $C_2$–$C_6$-alkenyl, $C_2$–$C_6$-alkinyl, chlorinated $C_1$–$C_6$-alkyl or phenyl-$C_1$–$C_5$-alkyl, $R_2$ is hydrogen or chlorine, $R_3$ is hydrogen or $C_1$–$C_6$-alkyl, $R_4$ is hydrogen, $C_1$–$C_6$-alkyl or phenyl which latter may also be substituted, $R_5$ is halogen, and $R_6$ is hydrogen or halogen. The compounds of the invention have a surprisingly high compatibility with rice, wheat, barley, oats, rye, and agricultural grasses when applied in a postemergence procedure. They also have a high activity against weeds of various resistant genera.

5 Claims, No Drawings

SUBSTITUTED CARBANILIC ACID ESTERS AND HERBICIDAL COMPOSITION CONTAINING SAME

This is a continuation of application Ser. No. 138,577, filed Apr. 8, 1980 and now abandoned.

BACKGROUND OF THE INVENTION

The invention relates to substituted carbanilic acid esters, a process for making the same and selective herbicidal compositions containing these compounds.

Herbicidal carbanilic acid esters, for instance, 3,4-dichlorocarbanilic acid methylester have already become known (West German Pat. No. 1,195,549). These prior art compounds, however, do not always have an adequate selective herbicidal action.

It is therefore an object of the present invention to furnish an agent which has a higher activity against weeds and at the same time a better compatibility for agricultural plants than prior art compounds of analogous constitution.

ESSENCE OF THE INVENTION

This object is met by a compound or composition characterized by containing one or more carbanilic acid esters of the formula

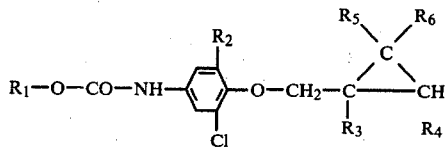

wherein
$R_1$ is $C_1$–$C_6$-alkyl, $C_2$–$C_6$-alkenyl, $C_2$–$C_6$-alkinyl, chlorinated $C_1$–$C_6$-alkyl or phenyl-$C_1$–$C_5$-alkyl,
$R_2$ is hydrogen or chlorine,
$R_3$ is hydrogen or $C_1$–$C_6$-alkyl,
$R_4$ is hydrogen, $C_1$–$C_6$-alkyl, or is phenyl which may also be substituted,
$R_5$ is halogen, and
$R_6$ is hydrogen or halogen.

The compounds of the invention have a surprisingly high compatibility with rice, wheat, barley, oats, rye, and agricultural grasses when applied in a postemergence procedure.

They also have a high activity against weeds of the genera: Sinapis, Brassica, Chenopodium, Atriplex, Solanum, Allium, Cucumis, Stellaria, Senecio, Matricaria, Lamium, Centaurea, Amaranthus, Chrysanthemum, Ipomoea, Polygonum, Echinochloa, Setaria, Digitaria, Valerianella, Digitalis, Trifolium, Portulaca, Papaver, Kochia, Gypsophila, Lactuca, Cheiranthus, Euphorbia, Linum, Datura, and Cichorium.

To control these seed weed it is in general sufficient to use amounts from 0.5 up to a maximum of 5 kg of active agent per about 2.5 acres (1 hectare). The compounds of the invention when thus applied have a clearly selective action in agricultural plantations involving wheat, barley, oats, rye, potatoes and rice.

The compounds can either be used by themselves or mixed with each other or mixed with other active agents. If desired, defoliants, other plant protection agents or pesticides may be added depending on the desired object.

If a broadening of the activity spectrum is intended, other herbicides may be added, for instance, suited for mixture with compounds of the invention are active agents from the groups of Triazines, Aminotriazoles, Anilides, Diazines, Uracils, aliphatic carboxylic acids and aryloxycarboxylic acids, hydrazides, amides, nitriles, esters of such carboxylic acids, carbamic acid and thiocarbamic acid ester, urea derivatives, 2,3,6-trichlorobenzyloxyisopropanol and rhodan containing agents, etc. Among the additives there may also be used nonphytotoxic additives which, with herbicides, result in a synergistic increase of activity such as wetting agents, emulsifiers, solution promoters and oily additions.

It is preferred to use the compounds or their mixture in the form of compositions such as powders, dusting agents, granulates, solvents, emulsions or suspensions. There are added to these compositions liquid and/or solid carrier materials or diluents and, if desired, wetting, adhesion, emulsion and/or dispersing supporting agents.

Suitable liquid carrier materials are for instance water, aliphatic and aromatic hydrocarbons, such as, benzene, toluene, xylene, cyclohexanone, isophorone, dimethylsulfoxide, dimethylformamide, and furthermore mineral oil fractions.

As solid carriers there may be used mineral earths, for instance, Tonsil, Silicagel, Talc, Kaolin, Attaclay, limestone, silicic acid and plant products, for instance flours. If it is desired to have a surface active agent there may be used, for instance, Calciumlignosulfonate, Polyoxyethylene-alkylphenol ethers, Naphthalene sulfonic acids and their salts, Phenolsulfonic acids and their salts, formaldehyde condensation products, fatty alcohol sulfates as well as substituted benzosulfonic acids and their salts. The proportion of the active agent or agents in the compositions can be varied within a broad range. For instance the compositions may contain about 10 to 90% by weight of active agent, about 90 to 10% by weight of liquid or solid carrier material and, if desired, up to 20% by weight of surface active agents in which latter case the carrier materials are correspondingly reduced.

The application of the composition can be effected in conventional form, for instance with water as carrier material in spray amounts of about 100 to 1000 liters per about 2.5 acres. The compounds may be used in the socalled low volume and ultra low volume procedure as well as in the form of so-called microgranulates.

Among the compounds of the invention a particularly good selective herbicidal action is possessed by those in which in the above given general formula the various radicals have the following meaning:
$R_1$ methyl, ethyl, propyl, isopropyl, allyl, 2-methyl-2-propenyl, 2-propinyl, 2-chloroethyl or benzyl,
$R_2$ is hydrogen or chlorine,
$R_3$ is hydrogen, methyl or ethyl,
$R_4$ is hydrogen, methyl or phenyl,
$R_5$ and $R_6$ are chlorine.

A particularly superior selective herbicidal activity have those compounds in which in the above general formula the radicals have the following significance:
$R_1$ methyl, ethyl, propyl, isopropyl, allyl or 2-methyl-2-propenyl,
$R_2$ hydrogen,
$R_3$ and $R_4$ hydrogen or methyl, and $R_5$ and $R_6$ chlorine.

PROCESS OF MAKING

The compounds of the invention can be made by various processes. The following are examples of these processes:

(a) Compounds of the formula

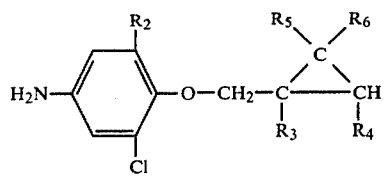

are reacted with compounds of the formula

R₁—O—CO—Cl dissolved in a solvent, for instance, acetic acid ester and water and in the presence of equimolar amounts of an inorganic base for instance sodium hydroxide, magnesium oxide, sodium- or potassium carbonate or a tertiary organic base such as triethylamine.

(b) Compounds of the formula

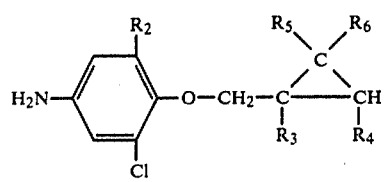

are at first reacted with phosgene to form the corresponding isocyanate which is then reacted with compounds of the formula

R₁OH dissolved in a solvent and in the presence of catalytic amounts of a base such as triethylamine.

The products of the invention are in both cases isolated by conventional methods. In both of these examples the radicals R₁ to R₆ have the meaning as given in the above general formula.

STARTING PRODUCT

The starting products for making the compounds of the invention are known or can be produced by obvious known methods.

For instance 2-halogeno-4-nitrophenol is at first alkylated in a polar aprotic solvent and in the presence of an equimolar amount of a base with the corresponding halomethyldihalogenocyclopropane. The alkylation of the phenol can also be carried out as a phase transfer catalyzed reaction.

The subsequent reduction of the aromatic nitro group can be effected by dissolving, for instance, 3-chloro-4-(2,2-dichlorocyclopropylmethoxy)-nitrobenzene in ethanol and followed by reduction of the nitro group at temperatures between 60° and 100° C. with a mixture of hydrazine and Raney nickel. There may then follow the partial reduction of a halogen atom present on the three-member ring.

EXAMPLES

The following examples will further illustrate the making of the compounds of the invention and will furnish further instances of specific compounds.

EXAMPLE 1

3-chloro-4-(2,2-dichlorocyclopropylmethoxy)-carbanilic acid methylester 17.4 g (0.1 mol) of 2-chloro-4-nitrophenol were dissolved in 100 ml dimethylformamide and were reacted in batches with a triturated mixture of 900 mg of sodium iodide and 16.3 g (0.11 mol) of potassium carbanate in the absence of water. Subsequently, 23 g (0.11 mol) of 1-bromomethyl-2,2-dichlorocyclopropane were added and the reaction mixture was stirred for 5 hours at 80° C.

After cooling the mass was stirred into 500 ml of ice water. The precipitated product was then removed by suction and washed with water.

The yield of 3-chloro-4-(2,2-dichlorocyclopropylmethoxy)-nitrobenzene was 23.3 g=79% of the theoretical value; and m.p.: 73°–74° C.

23.3 g (0.079 mol) of the thus obtained nitrobenzene were dissolved in 90 ml ethanol and were reacted with 14.2 ml (0.28 mol) of a 99% concentration hydrazine hydrate. To reduce the nitro group a total of about 3 g of Raney nickel were added in batches while stirring and cooling. The reaction temperature in this step should not exceed 60° C. The end of the reaction is apparent when the yellow color of the nitro compound disappears. After completion of the reaction there was added an additional amount of Raney nickel in order to destroy excess hydrazine. The still hot mixture was filtrated and the filtrate was concentrated to 10 to 15 ml. After adding about 10 ml of concentrated hydrochloric acid the hydrochloride precipitated. This was removed by suction and neutralized with aqueous sodium bicarbonate solution.

The free aniline was extracted with acetic acid ester, and the acetic acid ester phase was concentrated. There were obtained 3-chloro-4-(2,2-dichlorocyclopropylmethoxy)-aniline in an amount of 14.4 g=69% of the theoretical value.

14.20 g (0.053 mol) of the thus obtained aniline were dissolved in 100 ml acetic acid ester and were reacted with 25 ml water and 1.22 g (0.030 mol) of magnesium oxide.

4.54 ml (0.058 mol) of chloroformic acid methyl ester dissolved in 10 ml acetic acid ester were added dropwise and slowly while stirring. The reaction mixture was then heated up to a temperature of about 45° C. After 1 hour the reaction was complete. Excess magnesium oxide was caused to dissolve in dilute hydrochloric acid.

The organic phase was subsequently separated, washed neutral with water, dried on magnesium sulfate, and filtered. Trhe filtrate was concentrated until dryness.

m.p.: 78–79. C.

Yield: 14.5 g=83.9% of the theoretical value.

This product was the desired 3-chloro-4-(2,2-dichlorocyclopropylmethoxy)-carbanilic acid methylester.

EXAMPLE 2

3-chloro-4-(2,2-dichlorocyclopropylmethoxy)-carbanilic acid-n-propylester 47.0 g (0.176 mol) of 3-chloro-4-(2,2-dichlorocyclopropylmethoxy)-aniline were dissolved in 700 ml toluene. Upon exclusion of all moisture and vigorous stirring gaseous HCl was then introduced until the aniline was completely converted to the hydrochloride. The reaction time was about 30 minutes. The mixture was then heated to 80° to 90° C. and a faint current of phosgene was introduced while continuously stirring. The reaction temperature in this step was maintained at 80° to 90° C. After about 2 hours the hydrochloride had been converted completely to the isocyanate.

After the reaction was complete, that is the solution was clear, the toluene was distilled off in a water jet vacuum. The residue was then fractionated in an oil pump vacuum. B.p. 0.2=145° to 147° C.

The yield in 3-chloro-4-(2,2-dichlorocyclopropylmethoxy)-phenyl-isocyanate was 28 g=54% of the theoretical value.

8.0 g (0.0273 mol) of the just formed cyanate were then dissolved in 100 ml of absolute diethylether and were reacted with 3 drops of triethylamine. 2.1 ml (0.0273 mol) of n-propanol were then added dropwise in 10 ml of absolute diethylether at room temperature and while stirring and excluding all moisture.

To complete the reaction the mass was heated under reflux for about 2 hours. The ether was subsequently distilled off and the crude product was recrystallized from acetic acid ester/hexane. There was obtained 3-chloro-4-(2,2-dichlorocyclopropylmethoxy)-carbanilic acid-n-propylester in an amount of 9.20 g=95% of the theoretical value; m.p.: 57°–59° C.

In an analogous manner there were obtained the following additional compounds of the invention.

| Compound | Physical constants |
| --- | --- |
| 3-chloro-4-(2,2-dichlorocyclopropylmethoxy)-carbanilic acid-(2-methyl-2-propenyl)-ester | m.p.: 43–45° C. |
| 3-chloro-4-(2,2-dichlorocyclopropylmethoxy)-carbanilic acid-allylester | m.p.: 57–59° C. |
| 3-chloro-4-(2,2-dichlorocyclopropylmethoxy)-carbanilic acid-isopropylester | m.p.: 52–54° C. |
| 3-chloro-4-(2,2-dichlorocyclopropylmethoxy)-carbanilic acid ethylester | m.p.: 96–98° C. |
| 3-chloro-4-(2,2-dichloro-1-methylcyclopropylmethoxy)-carbanilic acid methylester | m.p.: 74–75° C. |
| 3-chloro-4-(2,2-dichloro-1-methylcyclopropylmethoxy)-carbanilic acid ethylester | $n_D 20$: 1,5422 |
| 3-chloro-4-(2,2-dichloro-1-methylcyclopropylmethoxy)-carbanilic acid-n-propylester | $n_D 20$: 1,5390 |
| 3-chloro-4-(2,2-dichloro-1-methylcyclopropylmethoxy)-carbanilic acid-isopropylester | $n_D 20$: 1,5380 |
| 3-chloro-4-(2,2-dichloro-1-methylcyclopropylmethoxy)-carbanilic acid allylester | $n_D 20$: 1,5471 |
| 3-chloro-4-(2,2-dichloro-1-methylcyclopropylmethoxy)-carbanilic acid-(2-methyl-2-propenyl)-ester | $n_D 20$: 1,5513 |
| 3-chloro-4-(2,2-dichloro-3-methylcyclopropylmethoxy)-carbanilic acid methylester | $n_D 20$: 1,5533 |
| 3-chloro-4-(2,2-dichloro-3-methylcyclopropylmethoxy)-carbanilic acid ethylester | $n_D 20$: 1,5471 |
| 3-chloro-4-(2,2-dichloro-3-methylcyclopropylmethoxy)-carbanilic acid allylester | $n_D 20$: 1,5450 |
| 3-chloro-4-(2,2-dichloro-3-methylcyclopropylmethoxy)-carbanilic acid isopropylester | $n_D 20$: 1,5262 |
| 3,5-dichloro-4-(2,2-dichlorocyclopropylmethoxy)-carbanilic acid methylester | $n_D 20$: 1,5353 |
| 3-chloro-4-(2,2-dichloro-1-methylcyclopropylmethoxy)-carbanilic acid-benzylester | m.p.: 58–62° C. |
| 3-chloro-4-(2,2-dichloro-3-phenylcyclopropylmethoxy)-carbanilic acid methylester | m.p.: 105–107° C. |
| 3-chloro-4-(2,2-dichloro-3-phenylcyclopropylmethoxy)-carbanilic acid allylester | $n_D 20$: 1,5820 |
| 3,5-dichloro-4-(2,2-dichloro-1-methylcyclopropylmethoxy)-carbanilic acid ethylester | m.p.: 73–77° C. |
| 3,5-dichloro-4-(2,2-dichloro-1-methylcyclopropylmethoxy)-carbanilic acid isopropylester | m.p.: 119–121° C. |
| 3-chloro-4-(2,2-dichloro-3-phenylcyclopropylmethoxy)-carbanilic acid ethylester | $n_D 50$: 1,5769 |
| 3,5-dichloro-4-(2,2-dichloro-1-methylcyclopropylmethoxy)-carbanilic acid methylester | m.p.: 60–63° C. |
| 3-chloro-4-(2,2-dibromo-1-methylcyclopropylmethoxy)-carbanilic acid methylester | m.p.: 99–102° C. |
| 3-chloro-4-(2,2-dibromo-1-methylcyclopropylmethoxy)-carbanilic acid ethylester | $n_D 50$: 1,5650 |
| 3-chloro-4-(2,2-dibromo-1-methylcyclopropylmethoxy)-carbanilic acid allylester | $n_D 50$: 1,5716 |
| 3,5-dichloro-4-(2,2-dichloro-3-methylcyclopropylmethoxy)-carbanilic acid methylester | $n_D 50$: 1,5550 |
| 3,5-dichloro-4-(2,2-dichloro-3-methylcyclopropylmethoxy)-carbanilic acid ethylester | $n_D 50$: 1,5441 |
| 3,5-dichloro-4-(2,2-dichloro-3-methylcyclopropylmethoxy)-carbanilic acid allylester | $n_D 50$: 1,5489 |

The compounds of the invention have good solubility in acetone, acetic acid ethylester and alcohol. Their solubility in benzene is only limited and they are practically insoluble in saturated hydrocarbons and water.

USES AND ACTIVITY

The following examples will further illustrate the uses of the compounds and their respective activity.

EXAMPLE 3

The compounds listed below were sprayed in a hothouse as aqueous emulsions or suspensions in an amount of 5 kg of active agent per about 2.5 acres in a spray of 500 liter water per 2.5 acres. The plants were sprayed in a postemergence application and are listed below.

The treatment was evaluated 3 weeks later on a scale from 0=no effect to 4=complete destruction of the plants.

As the table shows there was obtained a complete destruction of the weeds, while the barley remained undamaged.

| Compounds | barley | Sinapis | Solanum | Setaria |
|---|---|---|---|---|
| 3-chloro-4-(2,2-dichlorocyclopropyl-methoxy)-carbanilic acid methylester | 0 | 4 | 4 | 4 |
| 3-chloro-4-(2,2-dichloro-1-methyl-cyclopropylmethoxy)-carbanilic acid methylester | 0 | 4 | 4 | 4 |
| 3-chloro-4-(2,2-dichlorocyclopropyl-methoxy)-carbanilic acid-(2-methyl-2-propenyl)-ester | 0 | 4 | 4 | 4 |
| 3-chloro-4-(2,2-dichlorocyclopropyl-methoxy)-carbanilic acid-n-propyl-ester | 0 | 4 | 4 | 4 |
| 3-chloro-4-(2,2-dichlorocyclopropyl-methoxy)-carbanilic acid allylester | 0 | 4 | 4 | 4 |
| 3-chloro-4-(2,2-dichlorocyclopropyl-methoxy)-carbanilic acid isopropyl-ester | 0 | 4 | 4 | 4 |
| 3-chloro-4-(2,2-dichlorocyclopropyl-methoxy)-carbanilic acid ethylester | 0 | 4 | 4 | 4 |
| 3-chloro-4-(2,2-dichloro-1-methyl-cyclopropylmethoxy)-carbanilic acid methylester | 0 | 4 | 4 | 4 |
| 3-chloro-4-(2,2-dichloro-1-methyl-cyclopropylmethoxy)-carbanilic acid allylester | 0 | 4 | 4 | 4 |
| 3-chloro-4-(2,2-dichloro-1-methyl-cyclopropylmethoxy)-carbanilic acid isopropylester | 0 | 4 | 4 | 4 |
| 3-chloro-4-(2,2-dichloro-1-methyl-cyclopropylmethoxy)-carbanilic acid-n-propylester | 0 | 4 | 4 | 4 |
| 3-chloro-4-(2,2-dichloro-1-methyl-cyclopropylmethoxy)-carbanilic acid-(2-methyl-2-propenyl)-ester | 0 | 4 | 4 | 4 |
| 3-chloro-4-(2,2-dichloro-3-methyl-cyclopropylmethoxy)-carbanilic acid methylester | 0 | 4 | 4 | 4 |
| 3-chloro-4-(2,2-dichloro-3-methyl-cyclopropylmethoxy)-carbanilic acid ethylester | 0 | 4 | 4 | 4 |
| 3-chloro-4-(2,2-dichloro-3-methyl-cyclopropylmethoxy)-carbanilic acid allylester | 0 | 4 | 4 | 4 |
| 3-chloro-4-(2,2-dichloro-3-methyl-cyclopropylmethoxy)-carbanilic acid isopropylester | 0 | 4 | 4 | 4 |
| 3-chloro-4-(2,2-dichloro-1-methyl-cyclopropylmethoxy)-carbanilic acid benzylester | 0 | 4 | 4 | — |
| 3-chloro-4-(2,2-dichloro-3-phenylcyclo-propylmethoxy)-carbanilic acid methylester | 0 | 4 | 4 | 4 |
| 3-chloro-4-(2,2-dichloro-3-phenyl-cyclopropylmethoxy)-carbanilic acid allylester | 0 | 4 | 4 | 4 |
| 3,5-dichloro-4-(2,2-cichloro-1-methyl-cyclopropylmethyl-cyclopropyl-methoxy)carbanilic acid ethylester | 0 | 4 | — | — |
| 3,5-dichloro-4-(2,2-dichloro-1-methyl-cyclopropylmethoxy)-carbanilic acid isopropylester | 0 | 4 | 4 | — |
| 3-chloro-4-(2,2-dichloro-3-phenylcyclo-propylmethoxy)-carbanilic acid ethyl-ester | 0 | 4 | 4 | 4 |
| 3,5-dichloro-(2,2-dichloro-1-methyl-cyclopropylmethoxy)-carbanilic acid methylester | 0 | 4 | 4 | — |
| 3-chloro-4-(2,2-dibromo-1-methylcyclo-propylmethoxy)-carbanilic acid methyl-ester | 0 | 4 | 4 | 4 |
| 3-chloro-4-(2,2-dibromo-1-methylcyclo-propylmethoxy)-carbanilic acid ethyl-ester | 0 | 4 | 4 | 4 |
| 3-chloro-4-(2,2-dibromo-1-methylcyclo-propylmethoxy)-carbanilic acid allyl-ester | 0 | 4 | 4 | 4 |
| 3,5-dichloro-4-(2,2-dichloro-3-methyl-cyclopropylmethoxy)-carbanilic acid methylester | 0 | 4 | 4 | — |
| 3,5-dichloro-4-(2,2-dichloro-3-methyl-cyclopropylmethoxy)-carbanilic acid ethylester | 0 | 4 | 4 | — |
| 3,5-dichloro-4-(2,2-dichloro-3-methyl-cyclopropylmethoxy)-carbanilic acid allylester | 0 | 4 | 4 | — |
| Untreated | 0 | 0 | 0 | 0 |

EXAMPLE 4

The plants listed below were treated in a postemergence application in a hothouse with the compounds also listed in the form of aqueous emulsions or suspensions in an amount of 3 kg of active agent per about 2.5 acres. The compositions were sprayed in a uniform manner on the plants.

An evaluation was effected 3 weeks after the treatment on a scale from 0 to 10 in which 0=total destruction and 10=no damage to the plants. In this evaluation the compounds of the invention showed a high compatibility which was completely absent in the comparison compound.

| Compounds | rice | wheat | barley |
|---|---|---|---|
| 3-chloro-4-(2,2-dichlorocyclo-propylmethoxy)-carbanilic acid methylester | 10 | 10 | 10 |
| 3-chloro-4-(2,2-dichloro-1-methyl-cyclopropylmethoxy)-carbanilic acid methylester | 10 | 10 | 10 |
| Comparison compound (West German Patent 1 195 549) 3,4-dichloro-carbanilic acid methylester | 6 | 5 | 4 |
| Untreated | 10 | 10 | 10 |

EXAMPLE 5

The plants listed below were sprayed in a hothouse after emergence with the compounds of the invention in the form of aqueous emulsions or suspensions in an amount of 0.3 kg of active agent per about 2.5 acres. The compositions were applied in a uniform manner to the plants.

An evaluation was effected 3 weeks after treatment on a scale from 0 to 10 in which 0=total destruction and 10=no damage to the plants.

As appears, the compounds of the invention generally developed an excellent activity while this was not the case with the comparison compound.

| | 3-chloro-4-(2,2-dichlorocyclo-propylmethoxy)-carbanilic acid-methylester | 3-chloro-4-(2,2-dichloro-1-methylcyclopropylmethoxy)-carbanilic acid-methylester | Comparison Compound (West German Patent 1 195 549) 3,4-dichloro-carbanilic acid-methylester |
|---|---|---|---|
| Valerianella | 0 | 0 | 3 |
| Digitalis | 0 | 0 | 1 |
| Trifolium | 0 | 0 | 8 |
| Portulaca | 0 | 0 | 1 |

-continued

| | 3-chloro-4-(2,2-dichlorocyclo-propylmethoxy)-carbanilic acid-methylester | 3-chloro-4-(2,2-dichloro-1-methylcyclopropylmethoxy)-carbanilic acid-methylester | Comparison Compound (West German Patent 1 195 549) 3,4-dichloro-carbanilic acid-methylester |
|---|---|---|---|
| *Papaver rhoeas* | 0 | 0 | 3 |
| Kochia | 0 | 0 | 0 |
| Gypsophila | 0 | 0 | 0 |
| Lactuca | 0 | 0 | 3 |
| *Escholtzia calafornica* | 1 | 0 | 8 |
| *Cheiranthus cheiri* | 2 | 1 | 8 |
| Euphorbia | 5 | 5 | 10 |
| Linum | 0 | 0 | 4 |
| *Datura Stramonium* | 0 | 0 | 0 |
| *Cichorium intybus foliosum* | 0 | 0 | 3 |
| *Ipomea tricolor* | 1 | 1 | 6 |
| *Setaria faberi* | 5 | 3 | 8 |
| Brassica | 0 | 0 | 7 |
| Chenopodium | 0 | 0 | 3 |
| Cellium | 0 | 0 | 6 |
| Cucumis | 0 | 0 | 6 |
| Medicago | 1 | 3 | 7 |
| Phaseolus | 2 | 2 | 8 |
| *Matricaria ch.* | — | 2 | 7 |
| *Lamium a.* | 0 | 0 | 3 |
| *Chrysanthemum a.* | 0 | 0 | 7 |
| *Echinochloa c.g.* | 0 | 0 | 4 |
| *Setaria i.* | 4 | 2 | 7 |
| *Digitaria s.* | 0 | 0 | 6 |
| UNTREATED | 10 | 10 | 10 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A selective herbicidal composition comprising at least one carbanilic acid ester selected from the group consisting of 3-chloro-4-(2,2-dichlorocyclopropylmethoxy)-carbanilic acid-methylester, 3-chloro-4-(2,2-dichloro-1-methylcyclopropylmethoxy)-carbanilic acid-methylester and 3-chloro-4-(2,2-dichloro-1-methycyclopropylmethoxy)-carbanilic acid-benzylester in an amount of 10 to 90 percent by weight and an inert liquid or solid carrier material in amount of 90 to 10 percent by weight.

2. The composition of claim 1 which includes up to 20% by weight of a surface active agent with a corresponding reduction of the solid or liquid carrier materials.

3. 3-chloro-4-(2,2-dichloro-1-methylcyclopropylmethoxy)-carbanilic acid-methylester.

4. 3-chloro-4-(2,2-dichloro-1-methylcyclopropylmethoxy)-carbanilic acid-benzylester.

5. 3-chloro-4-(2,2-dichlorocyclopropylmethoxy)-carbanilic acid-methylester.

* * * * *